(12) United States Patent
Paulsen et al.

(10) Patent No.: US 12,186,492 B2
(45) Date of Patent: Jan. 7, 2025

(54) LIGHTING DEVICE

(71) Applicants: Gary Paulsen, Chicago, IL (US);
David Basken, Chicago, IL (US);
Matthew Muller, Chicago, IL (US)

(72) Inventors: Gary Paulsen, Chicago, IL (US);
David Basken, Chicago, IL (US);
Matthew Muller, Chicago, IL (US)

( * ) Notice: Subject to any disclaimer, the term of this patent is extended or adjusted under 35 U.S.C. 154(b) by 0 days.

(21) Appl. No.: 18/454,340

(22) Filed: Aug. 23, 2023

(65) Prior Publication Data

US 2023/0390518 A1    Dec. 7, 2023

Related U.S. Application Data

(63) Continuation of application No. PCT/US2022/077874, filed on Oct. 11, 2022.

(60) Provisional application No. 63/278,680, filed on Nov. 12, 2021.

(51) Int. Cl.
*A61M 21/00* (2006.01)
(52) U.S. Cl.
CPC ..... *A61M 21/00* (2013.01); *A61M 2021/0044* (2013.01)
(58) Field of Classification Search
CPC .......... A61M 21/00; A61M 2021/0044; A61M 2021/0005; A61M 21/02
See application file for complete search history.

(56) References Cited

U.S. PATENT DOCUMENTS

| 10,993,298 B2 | 4/2021 | Paulsen et al. | |
| 2006/0136018 A1* | 6/2006 | Lack | A61M 21/00 |
| | | | 607/88 |
| 2010/0254129 A1 | 10/2010 | Le Toquin et al. | |
| 2016/0158486 A1* | 6/2016 | Colbaugh | A61M 21/00 |
| | | | 607/88 |

OTHER PUBLICATIONS

Wisowaty et al., "Temporal modulation sensitivity of the blue mechanism: measurements made without chromatic adaptation.", Vision Research, 1980, 20(11), 895-909.
Nakano et al., "Color fusion and flicker fusion frequencies using tritanopic pairs.", Vision Research, 1992, 32(8), 1417-1423.

* cited by examiner

*Primary Examiner* — Samuel G Gilbert
(74) *Attorney, Agent, or Firm* — McDonnell Boehnen Hulbert & Berghoff LLP (57) ABSTRACT

A method includes emitting a first light having a first color that is on a first Tritan confusion line defined by a Tritan copunctual point and emitting a second light having a second color that is on a second Tritan confusion line defined by the Tritan copunctual point. The second light is emitted out of phase with the first light, and the first Tritan confusion line, the Tritan copunctual point, and the second Tritan confusion line form an angle that is less than 10 degrees.

20 Claims, 6 Drawing Sheets

LIGHTING DEVICE

CROSS REFERENCE TO RELATED APPLICATIONS

The present application is a bypass continuation of and claims priority to international application PCT/US2022/077874, filed on Oct. 11, 2022, which claims priority to U.S. provisional application No. 63/278,680, filed on Nov. 12, 2021, the contents of both of which are hereby incorporated by reference.

The present application incorporates by reference the entire disclosures of the following applications: U.S. application Ser. No. 16/708,563 filed on Dec. 10, 2019, U.S. application Ser. No. 16/545,853 filed on Aug. 20, 2019, U.S. application Ser. No. 16/545,750 filed on Aug. 20, 2019, U.S. application Ser. No. 15/943,210 filed on Apr. 2, 2018, International Application No. PCT/US2018/020395 filed on Mar. 1, 2018, U.S. Provisional Application No. 62/546,475 filed on Aug. 16, 2017, U.S. Provisional Application No. 62/508,286 filed on May 18, 2017, U.S. application Ser. No. 17/100,536 filed on Nov. 20, 2020, U.S. Provisional Application No. 63/024,806 filed on May 14, 2020, and U.S. Provisional Application No. 62/939,037 filed on Nov. 22, 2019.

BACKGROUND

It may be useful to alter a person's circadian rhythm or "sleep cycle" for reasons such as jet lag or adjustment to non-traditional work shifts. A person's circadian rhythm is principally governed by the suprachiasmatic nucleus (SCN), which is a small region within the brain's hypothalamus. Previous methods for altering a person's circadian rhythm have generally involved direct stimulation of the light-sensitive protein melanopsin within intrinsically photosensitive retinal ganglion cells (ipRGCs) that make up about 1% of retinal ganglion cells within the retina. It is thought that illumination of the retina with blue light (e.g, a narrow range of wavelengths around about 480 nanometers) causes melanopsin excited within a person's ipRGCs to stimulate the SCN via neural pathways, thereby altering the person's circadian rhythm (e.g., delaying the onset of tiredness). However, due to the ipRGCs' relatively low photosensitivity, their relatively sparse presence within the retina, and slow photoactive response, such methods may undesirably involve illuminating the retina with intensities that are unpleasant or even painful for relatively long periods of time.

SUMMARY

One aspect of the disclosure is a method comprising: emitting a first light having a first color that is on a first Tritan confusion line defined by a Tritan copunctual point; and emitting a second light having a second color that is on a second Tritan confusion line defined by the Tritan copunctual point, wherein the second light is emitted out of phase with the first light, and wherein the first Tritan confusion line, the Tritan copunctual point, and the second Tritan confusion line form an angle that is less than 10 degrees.

Another aspect of the disclosure is a control system configured to cause a lighting device to perform functions comprising: emitting a first light having a first color that is on a first Tritan confusion line defined by a Tritan copunctual point; and emitting a second light having a second color that is on a second Tritan confusion line defined by the Tritan copunctual point, wherein the second light is emitted out of phase with the first light, and wherein the first Tritan confusion line, the Tritan copunctual point, and the second Tritan confusion line form an angle that is less than 10 degrees.

Another aspect of the disclosure is a lighting device comprising: a light source assembly; and a control system configured to cause the light source assembly to perform functions comprising: emitting a first light having a first color that is on a first Tritan confusion line defined by a Tritan copunctual point; and emitting a second light having a second color that is on a second Tritan confusion line defined by the Tritan copunctual point, wherein the second light is emitted out of phase with the first light, and wherein the first Tritan confusion line, the Tritan copunctual point, and the second Tritan confusion line form an angle that is less than 10 degrees.

By the term "about" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The features, functions, and advantages that have been discussed can be achieved independently in various examples or may be combined in yet other examples further details of which can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying Figures.

DETAILED DESCRIPTION

As discussed above, current methods for altering circadian rhythm via direct stimulation of melanopsin within intrinsically photosensitive retinal ganglion cells (ipRGCs) are often inconvenient, unpleasant, and/or somewhat ineffective. Accordingly, improved devices and methods for altering circadian rhythm are disclosed herein.

Circadian rhythm can be altered more conveniently and efficiently via stimulation of S-cones, M-cones, and L-cones within the retina, which causes indirect stimulation of ipRGCs that are downstream of the cones along neural pathways. Whereas previous methods involve illuminating ipRGCs with blue light (e.g., $\lambda\sim480$ nm) to optimize melanopsin photoactivity, the methods disclosed herein generally involve illuminating a retina with wavelengths designed to stimulate S-cones having a maximum photosensitivity at about 419 nm, M-cones having a maximum photosensitivity at about 530 nm, and/or L-cones having a maximum photosensitivity at about 559 nm.

More specifically, the stimulation of cones, which have a dense presence within the retina and higher photosensitivity when compared to ipRGCs, can cause more efficient excitation of ipRGCs than direct stimulation of the ipRGCs via sunlight. This indirect excitation of the ipRGCs can cause stimulation of the suprachiasmatic nucleus (SCN). This method of indirectly exciting ipRGCs via excitation of cones can be implemented at times when a person's circadian rhythm is more susceptible to change.

For example, the method performed by the lighting device can be implemented at times when one or more persons in a position to see the light emitted by the lighting device are nearing or have recently experienced a daily minimum in their respective circadian rhythms. For example, when the light emitted by the lighting device is seen by a person that is nearing (e.g., within 4 hours before) his or her sleepiest time of the day, the light will tend to delay the onset of sleepiness. For many people, the sleepiest point of the day ranges from about midnight to 2:30 AM (0:00 to 2:30). On the other hand, when the light emitted by the lighting device is seen by a person that has recently experienced (e.g., within 4 hours after) his or her sleepiest time of the day, the light will tend to advance the onset of sleepiness.

The ipRGCs, like all retinal ganglion cells, are driven by upstream cone photoreceptors. Hence, sharp increases and decreases (deltas) in illuminance incident on the cones robustly drive signaling of ipRGCs. For example, the activity of ipRGCs (and the resultant activity of the downstream SCN) is maximized in response to sharp increases in photoabsorption by M-cones (e.g., green light) and L-cones (e.g., red light), and sharp decreases in photoabsorption by S-cones (e.g., violet light).

More particularly, a lighting device can emit two colors of light oscillating fast enough so that to a human they appear steady (e.g., as one steady color), but slow enough that cone photoreceptors still respond and drive activity through the ipRGCs and on to the circadian centers. Thus, a lighting device that is useful as general home or workplace lighting can be used to regulate human Circadian rhythms.

Disclosed examples will now be described more fully hereinafter with reference to the accompanying Drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Figure 1:
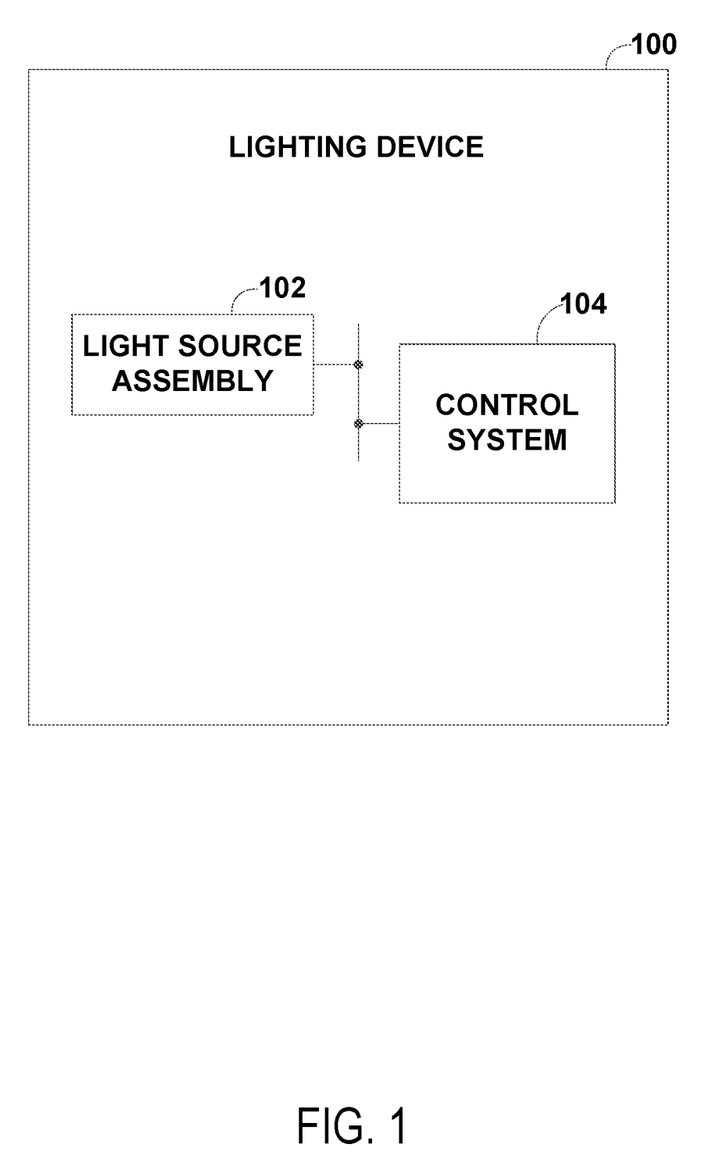
FIG. 1 is a block diagram of a lighting device, according to an example.

FIG. 1 depicts a lighting device 100 that includes a light source assembly 102 and a control system 104. In some examples, the light source assembly 102 may include one or more light sources such as light emitting diodes (LEDs), lasers, organic light emitting diodes (OLEDs) incandescent bulbs, or halogen bulbs, but other examples are possible.

The control system 104 may take the form of any combination of software and/or hardware that is configured to cause the light source assembly 102 and/or the lighting device 100 to perform any of the functions that are described herein. For example, the control system 104 may include one or more Boolean circuits, programmable logic controllers (PLCs), and/or special purpose circuits configured to provide electrical power and/or control signals to the light source assembly 102 for performing any of the functions described herein. Additionally or alternatively, the control system 104 may include one or more processors and a computer readable medium storing instructions that, when executed by the processors, cause the light source assembly 102 and/or the lighting device 100 to perform any of the functions described herein. The control system 104 may additionally include a signal generator.

In various examples, the lighting device 100 may be incorporated into or take the form of a wearable device, goggles, a headband, armwear, wristwear, or a therapeutic wearable device configured to shine light onto a subject's retina. In some examples, the lighting device 100 is incorporated into a vehicle such as an automobile, an airplane, a helicopter, a boat, a ship, or a train. The lighting device 100 could also be incorporated into a dashboard, an accent lighting unit, a cabin general lighting unit, or a headlight unit. In various examples, the lighting device 100 is incorporated into a display unit such as a cell phone, a tablet computer, a monitor, or a television. The lighting device 100 could also be incorporated into a lighting unit such as a lamp, a nightlight, a chandelier, or an overhead lighting unit.

In some embodiments, the lighting device 100 may take the form of a white light source having a color rendering index of greater than 70 as compared to daylight, a blackbody, or another lighting reference standard. The term "white light" as used herein may refer to any polychromatic light having a color rendering index greater than 70 as defined by the International Commission on Illumination (CIE) Ra scale. Such white light may include non-zero intensities throughout the visible spectrum of 400-700 nm. As such, a "white light source" may include any light source configured to generate white light as described above. The term "color rendering index" (CRI) as used herein may also be generally defined with reference to the CIE Ra scale.

Figure 2:
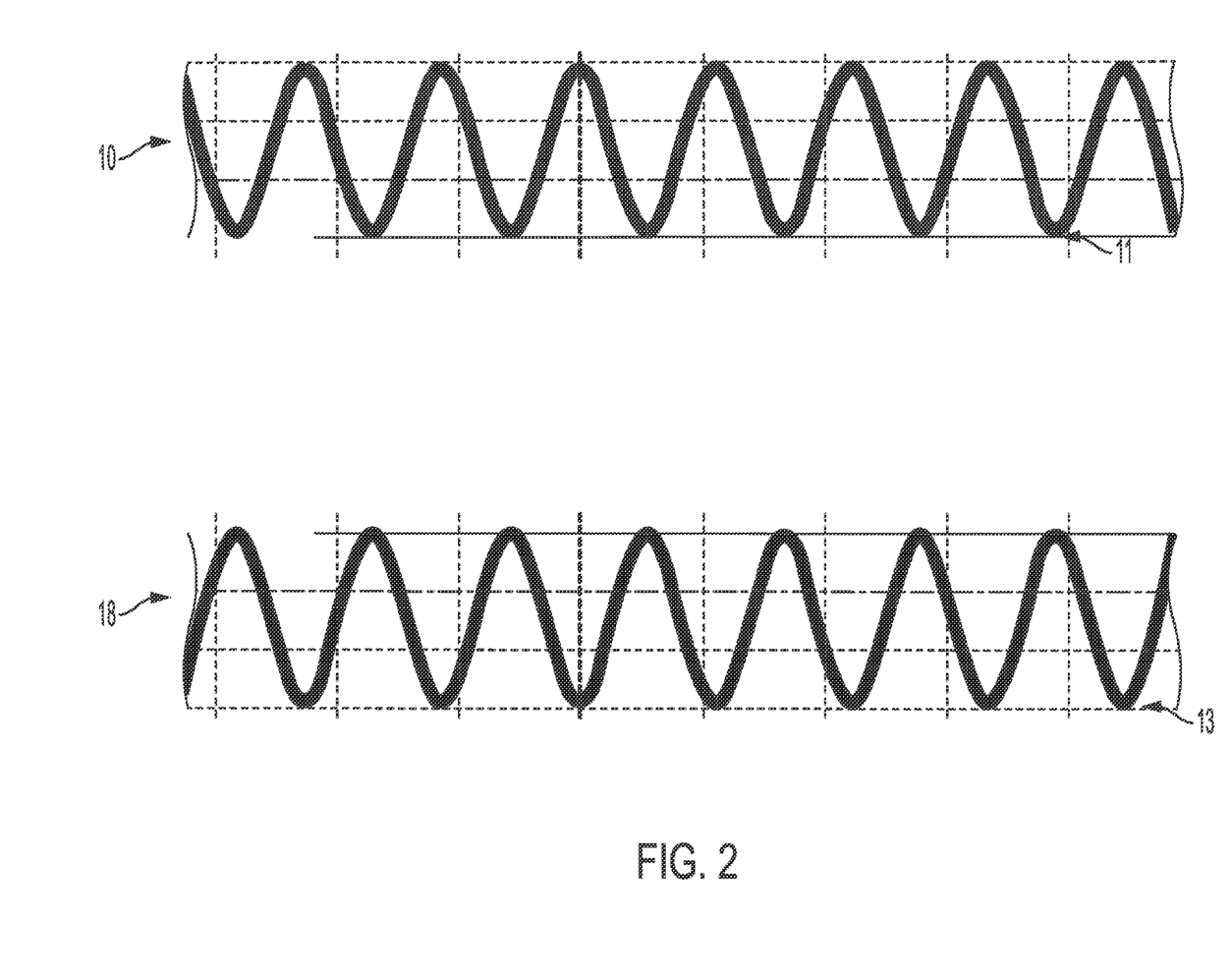
FIG. 2 shows intensity waveforms of a first light and a second light, according to an example.

FIG. 2 depicts two lights emitted by the lighting device 100. The lighting device 100 and related methods disclosed herein can be used to cause advancement or delay of a person's circadian cycle for various purposes. Such methods can be performed to treat a subject afflicted with seasonal affective disorder (SAD) or another mood disorder, such as depression, bipolar disorder, or dysthymia. Disrupted or irregular sleep can also affect those suffering with cancer and/or heart disease, and these methods can be used accordingly to counteract such effects.

The lighting device 100 emits a first light 10 and a second light 18. The lighting device 100 emits the second light 18 out of phase (e.g., 180 degrees out of phase) with the first light 10, as shown. In FIG. 2, the first light 10 and the second light 18 both have sinusoid waveforms, but the first light 10 and the second light 18 can take other forms as well such as a square wave, a sinusoidal wave, a sawtooth wave, a triangle wave, or any oscillating wave. The light source assembly 102 may include one or more first light sources configured to emit the first light 10 and one or more second light sources configured to emit the second light 18, but other examples are possible.

More specifically, FIG. 2 shows the respective oscillating intensities of the first light 10 and the second light 18, with the intensity of the first light 10 being out of phase (e.g., by 180 degrees) with the intensity of the second light 18. That is, the horizontal axes represent time and the vertical axes represent intensity of light. In some examples, the periodic minimum intensity 11 of the first light 10 and the periodic minimum intensity 13 of the second light 18 are both zero, but non-zero examples are possible as well for the minimum intensities of the first light 10 and the second light 18. In examples where the waveforms take non-sinusoidal forms, the first light 10 and the second light 18 can have equal duty cycles or unequal duty cycles.

The intensity of the first light 10 generally oscillates at the same frequency as the second light 18. For example, the common oscillating frequency of the first light 10 and the second light 18 can be within a range of 1 Hz to 50 Hz. In various examples, the common oscillating frequency of the first light 10 and the second light 18 is greater than 8 Hz, greater than 10 Hz, or greater than 15 Hz. Also, the common oscillating frequency of the first light 10 and the second light 18 can be within a range of 17 Hz to 21 Hz, or more specifically, substantially equal to 19 Hz or exactly equal to 19 Hz.

These oscillating frequencies can be useful because the flicker fusion frequency of human S-cones is approximately 8 Hz to 10 Hz. Thus, a display of lights oscillating at greater than 8 Hz to 10 Hz that have respective colors on a common Tritan confusion line can be used to excite human S-cones without the user perceiving a change in the color of the light emitted by the lighting device 100. An oscillation frequency of about 19 Hz can be useful as it is greater than the flicker fusion frequency of S-cones yet low enough that the S-cones can have a robust physiological response that is somewhat in sync with the oscillating first light 10 and second light 18. These phenomena are described in more detail below.

Figure 3:
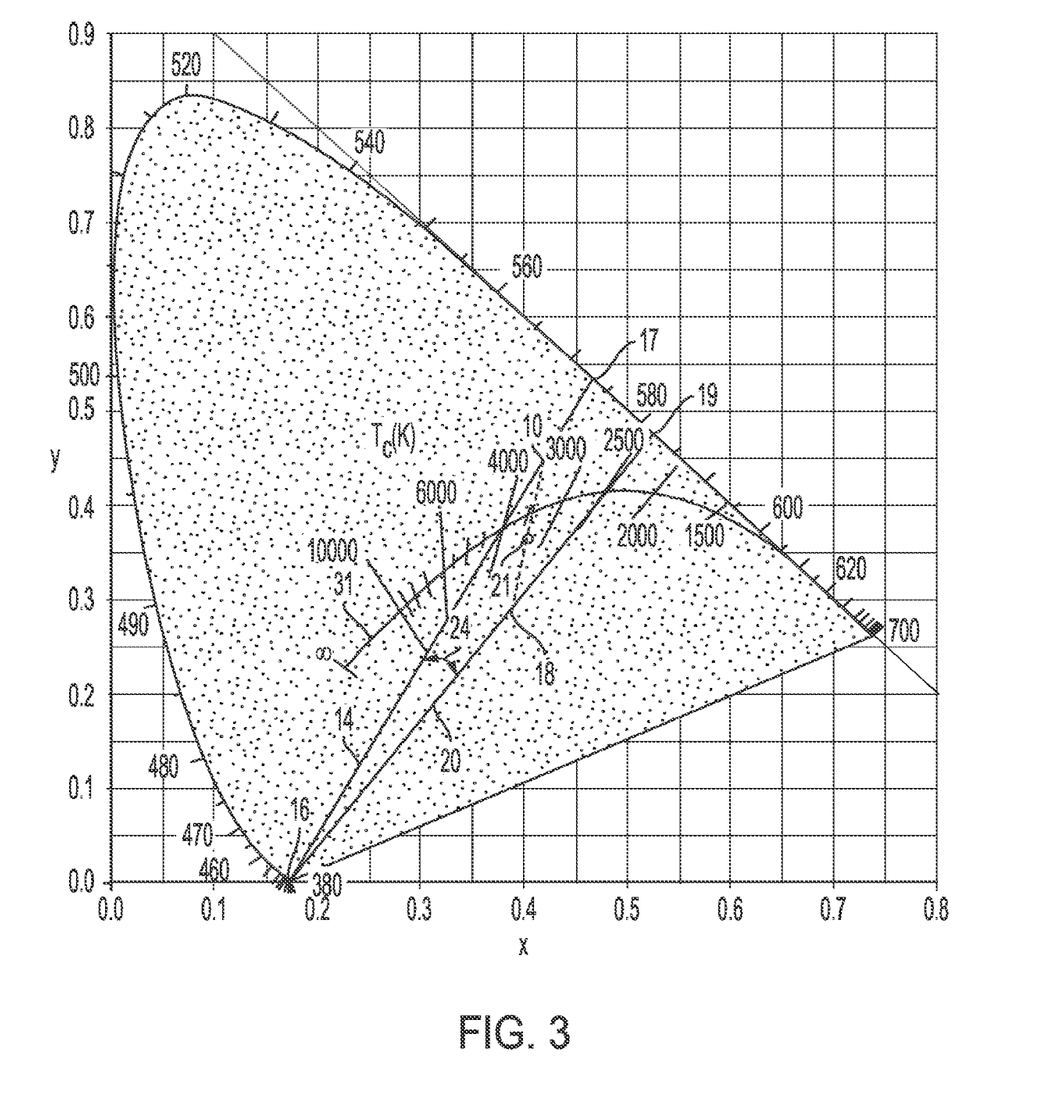
FIG. 3 shows colors of a first light and of a second light within a color space, according to an example.

FIG. 3 shows colors of the first light 10 and the second light 18 within the International Commission on Illumination (CIE) 1931 XYZ color space. The CIE 1931 XYZ color space is a visual representation of how colors perceived by humans relate to particular distributions of wavelengths in the electromagnetic visible spectrum. Other color spaces such as the CIE 1931 RGB color space or the 1976 CIELUV color space can also be used as the basis for defining the colors of the first light 10 and the second light 18.

As shown, the lighting device 100 emits the first light 10 having a first color that is on a first Tritan confusion line 14 defined by a Tritan copunctual point 16. In this example, the first color of the first light 10 is a non-spectral yellow. The first Tritan confusion line 14 has a first endpoint at the Tritan copunctual point 16 and a second endpoint 17 that is a spectral yellow color at a single wavelength of approximately 573 nm. The Tritan copunctual point 16 corresponds to a spectral violet color at a single wavelength of approximately 380 nm. Another way of defining the Tritan copunctual point 16 is that it has an x-coordinate of approximately and a y-coordinate of approximately zero within CIE 1931 XYZ. The Tritan copunctual point may be defined slightly differently in other color spaces.

The Tritan copunctual point 16 is the endpoint of an infinite number of Tritan confusion lines. That is, all Tritan confusion lines have an origin at the Tritan copunctual point 16. Any particular Tritan confusion line defines a spectrum of colors that vary only in how much they excite human S-cones. That is, any two colors located on the same Tritan confusion line will induce the same excitation of L-cones and M-cones, but induce different excitation of S-cones. Incidentally, this means that a person with Tritan colorblindness has difficulty distinguishing between two colors on the same Tritan confusion line.

The lighting device 100 also emits the second light 18 having a second color that is on a second Tritan confusion line 20 defined by the Tritan copunctual point 16. In this example, the second color of the second light 18 is a non-spectral pink. The second Tritan confusion line has a first endpoint at the Tritan copunctual point 16 and a second endpoint 19 that is a spectral yellowish orange color at a single wavelength of approximately 582 nm.

As noted above, the second light 18 is emitted out of phase with the first light 10. Additionally, the first Tritan confusion line 14, the Tritan copunctual point 16, and the second Tritan confusion line 20 form an angle 24 that is less than 10 degrees. In FIG. 3, the angle 24 is not necessarily drawn to scale and might correspond to Tritan confusion lines and/or colors that are different than those described above as examples. The angle 24 shown in FIG. 3 and the angle of 10 degrees serve merely as examples as well. In various examples, the angle 24 can be less than 5 degrees, less than 2.5 degrees, or less than 1 degree, with the lesser angles 24 providing less perceived color variation for the user.

Notably, FIG. 3 shows that two colors that are not quite aligned on the same Tritan confusion line can still provide a benefit to a user. For example, the out of phase oscillation of the first light 10 and the second light 18 will generally provide an oscillatory excitation to the user's S-cones and the user will generally only perceive a slight change in color via varying excitation of L-cones and M-cones. For instance, an oscillation frequency of 19 Hz is greater than the flicker fusion frequency of S-cones, so the user will generally not perceive the differing excitation of the S-cones that occurs. Instead, the user will generally perceive a time-averaged excitation of the S-cones (e.g., equivalent to an average color that represents a midpoint 21 between the first color of the first light 10 and the second color of the second light 18). However, the flicker fusion frequency of the L-cones and M-cones is greater than 19 Hz (e.g., approximately 40 Hz), so the user will generally perceive, at least to some degree, the time varying excitation of the L-cones and M-cones represented by the first light 10 and the second light 18. The excitation of the S-cones will generally induce a shift in the user's Circadian rhythm regardless of whether the excitation is perceived.

To provide an experience for the user that does not include a perceived oscillatory change of color, it is helpful to emit the first light 10 and the second light 18 such that they are on the same Tritan confusion line, such that the oscillatory frequency is greater than the flicker fusion frequency of S-cones, which are the only cones that could perceive the difference of two colors on the same Tritan confusion line.

Figure 4:
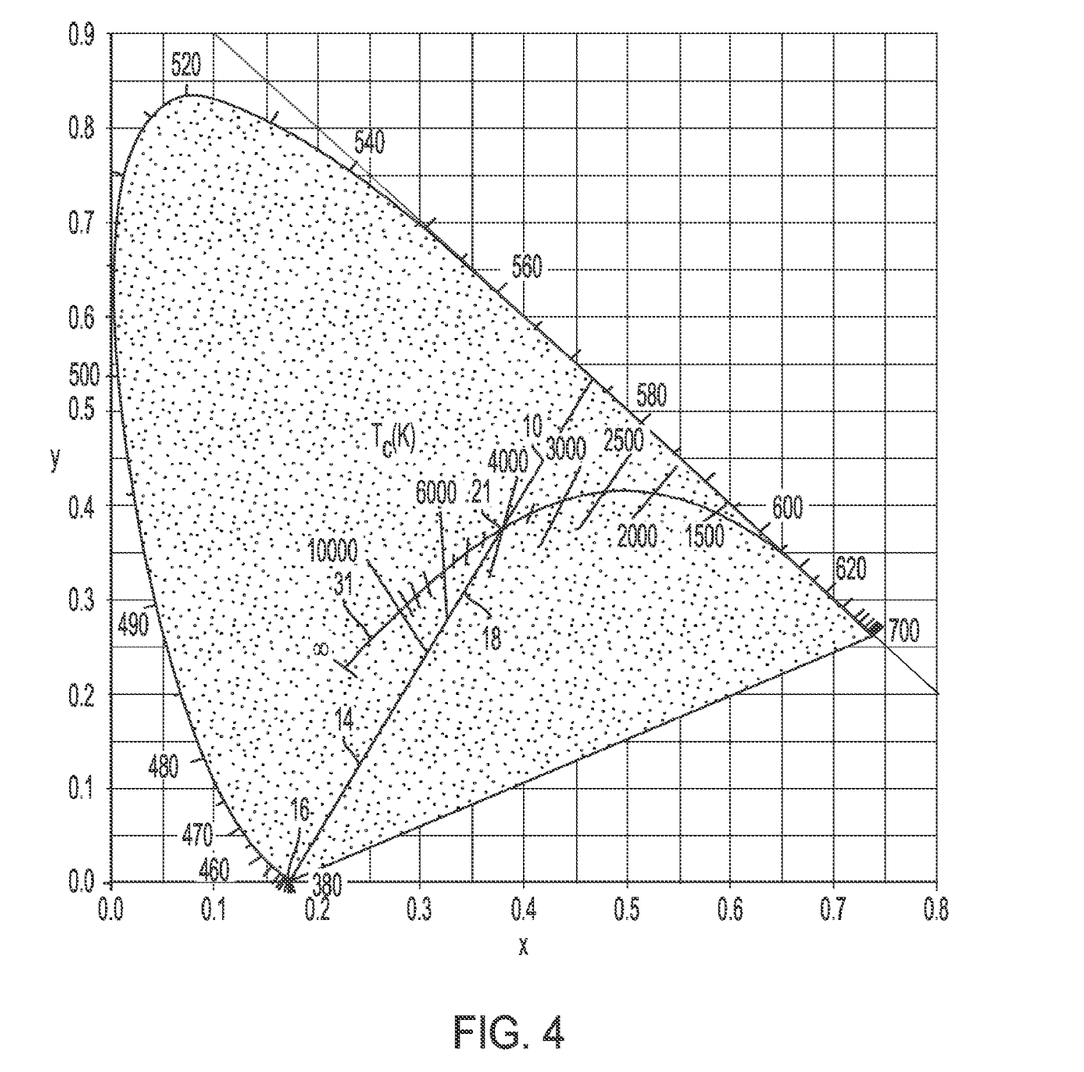
FIG. 4 shows colors of a first light and of a second light within a color space, according to an example.

FIG. 4 shows an example where the first color of the first light 10 and the second color of the second light 18 are on the same Tritan confusion line 14.

As shown, the lighting device 100 emits the first light 10 having a first color that is on the Tritan confusion line 14 defined by the Tritan copunctual point 16. In this example, the first color of the first light 10 is a non-spectral yellow. The lighting device 100 also emits the second light 18 having a second color that is on the Tritan confusion line 14. In this example, the second color of the second light 18 is a non-spectral greenish and/or yellowish white.

Notably, FIG. 4 shows that two colors that are aligned on the same Tritan confusion line can provide an increased benefit to a user. For example, the out of phase oscillation of the first light 10 and the second light 18 having colors that are on the common Tritan confusion line 14 will generally provide an oscillatory excitation exclusively to the user's S-cones, with the change in excitation of L-cones and M-cones being substantially zero. For instance, an oscillation frequency of 19 Hz is greater than the flicker fusion frequency of S-cones, so the user will generally not perceive the differing excitation of the S-cones that occurs. Instead, the user will perceive a time-averaged excitation of the S-cones (e.g., equivalent to an average color that represents a midpoint 21 on the Tritan confusion line 14 between the first color of the first light 10 and the second color of the second light 18). The excitation of the S-cones will generally induce a shift in the user's Circadian rhythm regardless of whether the excitation is perceived. As noted above, all colors on a common Tritan confusion line excite L-cones and M-cones at the same levels. Thus, even if the first light 10 and the second light 18 are oscillating below the flicker fusion frequency of the L-cones and the M-cones, it is irrelevant because no change in the excitation of the L-cones or M-cones is occurring. Thus, the user generally sees a color that does not change over time but the oscillating light induces a shift in Circadian rhythm.

As shown in FIG. 4, the first color of the first light 10 and the second color of the second light 18 are on opposite sides of a black body locus 31. The black body locus 31 represents a color spectrum of an incandescent black body at various temperatures in Kelvin. General purpose "white" room lighting often emits a color that is close to or on the black body locus 31. As shown, the midpoint 21 representing the average color of the first light 10 and the second light 18 is on the black body locus 31.

In various examples, it may be beneficial for the second color of the second light 18 to be at least 10%, at least 20%, at least 30%, at least 40%, or at least 50% closer to the Tritan copunctual point 16 than the first color of the first light 10. That is, a greater variation in the S-cone excitement caused by the first light 10 as compared to the second light 18 will generally cause a larger and/or quicker shift in Circadian rhythm.

Figure 5:
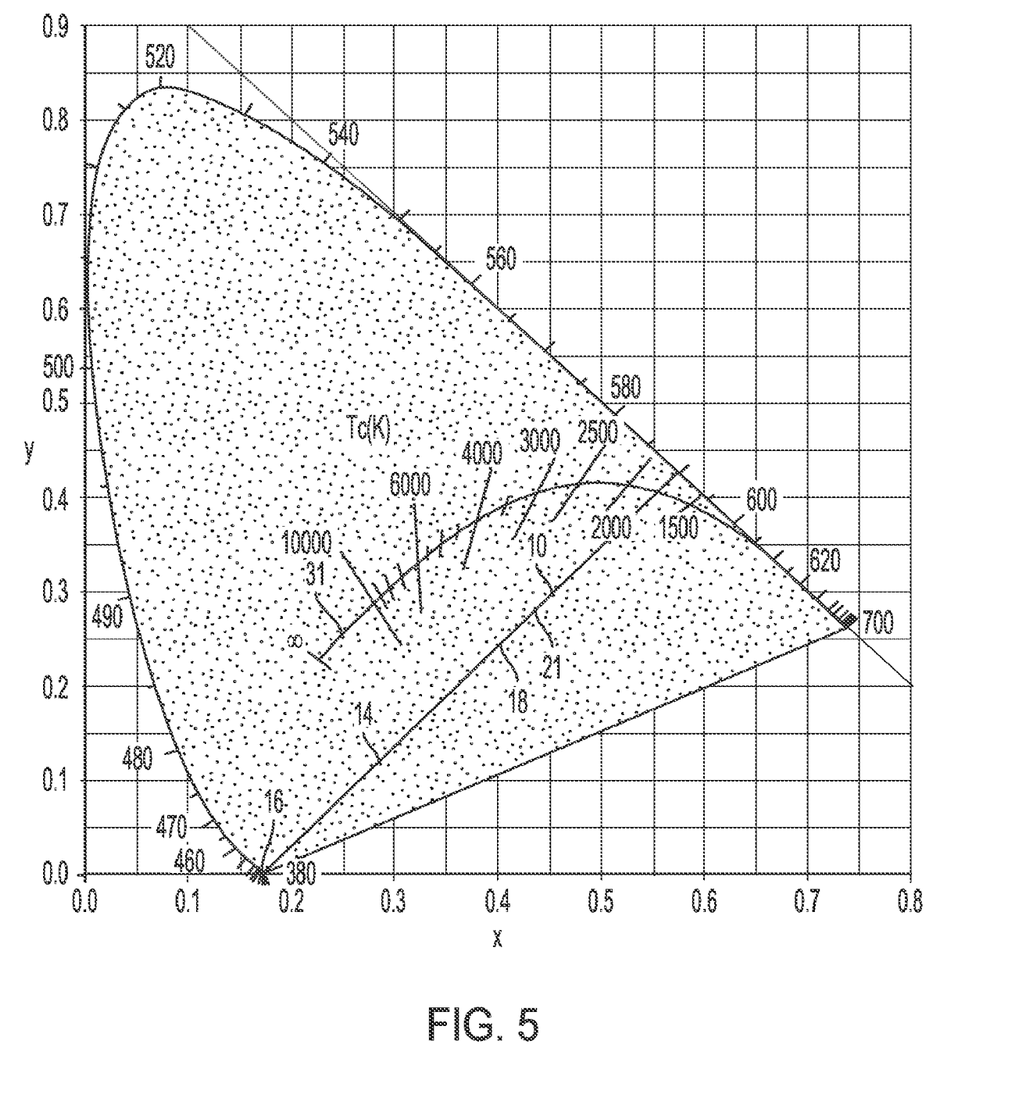
FIG. 5 shows colors of a first light and of a second light within a color space, according to an example.

FIG. 5 shows another example where the first color of the first light 10 and the second color of the second light 18 are on the same Tritan confusion line 14. However, in FIG. 5 the average color represented by the midpoint 21 is not located on the black body locus 31. Thus, instead of general purpose "white" lighting, FIG. 5 could represent a lighting device 100 configured to shift Circadian rhythm with a non-spectral pink mood lighting feature.

Figure 6:
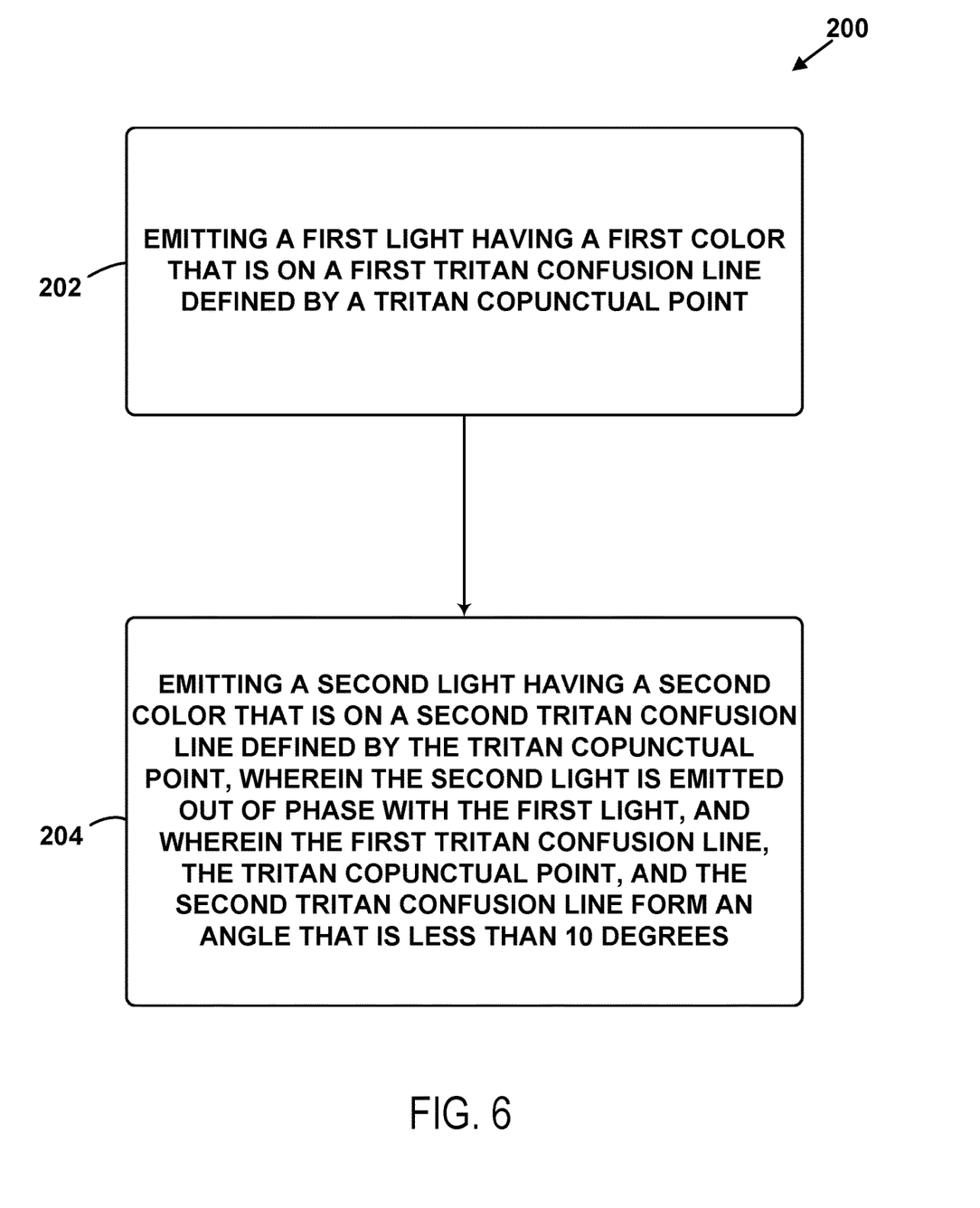
FIG. 6 is a block diagram of a method, according to an example.

FIG. 6 is a block diagram of a method 200. The method 200 is an example of a method that could be performed by the lighting device 100 as shown in FIGS. 1-5. As shown in FIG. 6, the method 200 includes one or more operations, functions, or actions as illustrated by blocks 202 and 204. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 202, the method 200 includes emitting the first light 10 having the first color that is on a first Tritan confusion line 14 defined by the Tritan copunctual point 16. Block 202 is described above with reference to FIGS. 1-5.

At block 204, the method 200 includes emitting the second light 18 having the second color that is on the second Tritan confusion line 20 defined by the Tritan copunctual point 16. The second light 18 is emitted out of phase with the first light 10. Also, the first Tritan confusion line 14, the Tritan copunctual point 16, and the second Tritan confusion line 20 form the angle 24 that is less than 10 degrees. Block 204 is described above with reference to FIGS. 1-5.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. A method comprising:
   emitting a first light having a first color that is on a first Tritan confusion line defined by a Tritan copunctual point having an x-coordinate of approximately 0.17045 and a y-coordinate of approximately zero within the International Commission on Illumination (CIE) 1931 XYZ color space; and
   emitting a second light having a second color that is on a second Tritan confusion line defined by the Tritan copunctual point, wherein the second light is emitted out of phase with the first light, and wherein the first Tritan confusion line, the Tritan copunctual point, and the second Tritan confusion line form an angle that is less than 10 degrees.

2. The method of claim 1, wherein the first Tritan confusion line, the Tritan copunctual point, and the second Tritan confusion line form the angle that is less than 5 degrees.

3. The method of claim 1, wherein the first Tritan confusion line, the Tritan copunctual point, and the second Tritan confusion line form the angle that is less than 1 degree.

4. The method of claim 1, wherein the first Tritan confusion line and the second Tritan confusion line are the same Tritan confusion line.

5. The method of claim 1, wherein the first color and the second color are on opposite sides of a black body locus.

6. The method of claim 1, wherein the first color and the second color are both non-spectral colors.

7. The method of claim 1, wherein the second color is at least 10% closer to the Tritan copunctual point than the first color.

8. The method of claim 1, wherein the second color is at least 20% closer to the Tritan copunctual point than the first color.

9. The method of claim 1, wherein the second color is at least 30% closer to the Tritan copunctual point than the first color.

10. The method of claim 1, wherein the second color is at least 40% closer to the Tritan copunctual point than the first color.

11. The method of claim 1, wherein emitting the second light comprises emitting the second light 180 degrees out of phase with the first light.

12. The method of claim 1, wherein emitting the first light comprises emitting the first light such that a first intensity of the first light oscillates at a first frequency and wherein emitting the second light comprises emitting the second light such that a second intensity of the second light oscillates at a second frequency that is equal to the first frequency.

13. The method of any of claim 12, wherein the first frequency is greater than 10 Hz.

14. The method of any of claim 12, wherein the first frequency is greater than 15 Hz.

15. The method of any of claim 12, wherein the first frequency is within a range of 17 Hz to 21 Hz.

16. The method of claim 1, wherein the x-coordinate is exactly 0.17045 and the y-coordinate is exactly zero within the International Commission on Illumination (CIE) 1931 XYZ color space.

17. A control system configured to cause a lighting device to perform functions comprising:
    emitting a first light having a first color that is on a first Tritan confusion line defined by a Tritan copunctual point having an x-coordinate of approximately 0.17045 and a y-coordinate of approximately zero within the International Commission on Illumination (CIE) 1931 XYZ color space; and
    emitting a second light having a second color that is on a second Tritan confusion line defined by the Tritan copunctual point, wherein the second light is emitted out of phase with the first light, and wherein the first Tritan confusion line, the Tritan copunctual point, and the second Tritan confusion line form an angle that is less than 10 degrees.

18. The control system of claim 17, wherein the x-coordinate is exactly 0.17045 and the y-coordinate is exactly zero within the International Commission on Illumination (CIE) 1931 XYZ color space.

19. A lighting device comprising:
    a light source assembly; and
    a control system configured to cause the light source assembly to perform functions comprising:
    emitting a first light having a first color that is on a first Tritan confusion line defined by a Tritan copunctual point having an x-coordinate of approximately 0.17045 and a y-coordinate of approximately zero within the International Commission on Illumination (CIE) 1931 XYZ color space; and
    emitting a second light having a second color that is on a second Tritan confusion line defined by the Tritan copunctual point, wherein the second light is emitted out of phase with the first light, and wherein the first Tritan confusion line, the Tritan copunctual point, and the second Tritan confusion line form an angle that is less than 10 degrees.

20. The lighting device of claim 19, wherein the x-coordinate is exactly 0.17045 and the y-coordinate is exactly zero within the International Commission on Illumination (CIE) 1931 XYZ color space.

* * * * *